United States Patent [19]

Brunsting

[11] Patent Number: 4,632,559
[45] Date of Patent: Dec. 30, 1986

[54] OPTICAL READHEAD

[75] Inventor: Albert Brunsting, Elkhart, Ind.

[73] Assignee: Miles Laboratories, Inc., Elkhart, Ind.

[21] Appl. No.: 704,767

[22] Filed: Feb. 21, 1985

Related U.S. Application Data

[63] Continuation-in-part of Ser. No. 445,203, Nov. 29, 1982, abandoned.

[51] Int. Cl.[4] .......................... G01J 3/51; G01N 21/47
[52] U.S. Cl. ....................................... 356/416; 356/446
[58] Field of Search ................ 356/402, 416, 445–448; 422/56, 57, 87, 68, 69; 436/43, 44, 164

[56] References Cited

U.S. PATENT DOCUMENTS

| | | | |
|---|---|---|---|
| 1,834,905 | 12/1931 | Sheldon | 356/448 |
| 3,999,864 | 12/1976 | Mutter | 356/416 |
| 4,033,698 | 7/1977 | Demsky et al. | 356/446 X |
| 4,115,067 | 9/1978 | Lyshkow | 436/44 X |
| 4,171,909 | 10/1979 | Kramer et al. | 356/448 X |

Primary Examiner—F. L. Evans
Attorney, Agent, or Firm—Roger N. Coe

[57] ABSTRACT

Reflectance apparatus is disclosed for obtaining measurement of nonspecular reflected light in which controlled light rays are directed by means of a lens and transmission path from a light source through a light trap to expose or illuminate a specimen and nonspecular reflected light is passed from the specimen through the light trap along a transmission path to one or more detectors where the nonspecular reflected light is measured.

9 Claims, 4 Drawing Figures

OPTICAL READHEAD

BACKGROUND OF THE INVENTION

Related Application

This is a continuation-in-part application of U.S. Ser. No. 445,203, filed Nov. 29, 1982, now abandoned.

Field of the Invention

The present invention relates to an optical readhead for reflectance devices and, more particularly, to a small, reliable and inexpensive optical readhead for illuminating a test device and measuring nonspecular reflected light.

Description of the Prior Art

The art of analytical chemistry has been greatly advanced since biochemistry began emerging as a primary scientific frontier, requiring increasingly sophisticated analytical methods and tools to solve problems, the solutions to which were never before attempted. Likewise the medical profession has lent impetus to the growth of analytical chemistry, with its desiderata of both high precision and speed in obtaining results. This remarkable progress has been still further spurred by industries such as brewing, chemical manufacturing and others.

To satisfy the needs of these expanding technologies a myriad of analytical procedures, compositions and apparatuses have evolved, including solution chemistry techniques, automated machinery and the so called "dip-and-read" type reagent strips.

Reagent strip test devices enjoy wide use in many analytical applications, especially in the chemical analysis of biological fluids, because of their relatively low cost, ease of use and speed in obtaining results. In medicine, for example, numerous physiological functions can be monitored merely by dipping reagent test devices into a sample of body fluid, such as urine or blood, and observing a detectable response such as change in color or change in the amount of light reflected from or absorbed by the test device. Many of these test devices produce a detectable response which is at least semi-quantitative, if not quantitative. Thus, by measuring the response after a predetermined time, the analyst can obtain not only a positive indication of the presence of a particular constituent in a test sample, but also an estimate of how much of the constituent is present. Such test devices provide the physician with a facile diagnostic tool as well as the ability to gauge the extent of disease or bodily malfunction.

Illustrative of such test devices currently in use are products available from the Ames Division of Miles Laboratories, Inc., under the trademarks CLINISTIX ®, MULTISTIX ®, DIASTIX ®, DEXTROSTIX ®, and others. Test devices such as these usually comprise one or more carrier matrices, such as an absorbent paper, having incorporated therewith a particular reagent or reactive system which manifests a color change in the presence of a specific sample component. Depending on the reactant system incorporated with a particular matrix, these devices can detect the presence of glucose, ketone bodies, bilirubin, urobilinogen, occult blood, nitrite, and other substances. The specific time range after contacting the test device with sample is indicative of the presence of a particular component and its concentration in the sample. Some of these test devices and their reactant systems are set forth in U.S. Pat. Nos. 3,123,443 (CLINISTIX ®); 3,212,855 (KETOSTIX ®); 3,184,668; 3,164,534 and 2,981,606 (DIASTIX ®); and 3,298,789; 3,164,534; 3,092,465 and 2,981,606 (DEXTROSTIX ®).

The development of automated instruments which eliminate the need for manual manipulation of the chemical reactants and which govern programmed readouts have greatly facilitated the use of such test devices, improving the reproducibility of the tests by substantially eliminating subjectivity of the user as a factor in obtaining a reliable measurement. Various reflectance instruments have been employed which use a light source and photoelectric cell or sensing means to determine color values by measuring the amount of light reflected from a colored surface illuminated by the reference light source. In order, however, to obtain reliable readings it has been necessary to position the light source and the sensing means in such a fashion as to minimize the affects of specular reflection, which occur at the surface of the test device being measured.

The importance of avoiding specular (i.e. mirror-like) reflections and obtaining measurement of nonspecular reflected light in a reflectance apparatus is particularly important in making reflectance measurements from the surface of diagnostic reagent strip test devices. As the area of a specimen decreases, detected light becomes more sensitive to surface heterogenities in the specimen if specular reflections are included. Thus, for a reagent matrix area of approximately 3/16 of an inch square, the signal obtained by illuminating the surface of the matrix material is very sensitive to surface irregularities. Specular reflections also carry information about the light source, such as color temperature in the case of an incandescent lamp. Color temperature information and surface heterogenities, which produce optical noise (N), can become mixed with the optical signal (S) which is carried by the diffusely reflected light.

In order to minimize adverse affects of specular reflection, e.g., results dependent upon the topography of a sample and/or the color temperature of the light source, instruments designed to measure diffuse reflectance have used having an axis of illumination which is normal of the specimen's plane and an axis of detection which is at an angle 45 degrees to normal of the specimen's plane, as in U.S. Pat. Nos. 3,604,815 and 3,907,503. Obviously, there is a reciprocal configuration with the axis of illumination being at an angle 45 degrees to the specimen's normal and the axis of detection parallel to the normal of the specimen's plane. Such configurations have required rather complicated arrangements of components and even the use of fiber optics to conveniently transmit light to a desired location. Others have proposed the use of multiple light sources positioned at an angle of 45 degrees to normal and collecting reflected light normal to the specimen, as in U.S. Pat. No. 4,279,514. The aforementioned geometries have been considered most important in making reflection measurements. See, for example, the International Commission on Illumination publication CIE No. 44(TC2.3) 1979 entitled "Absolute Methods for Reflectance Measurements".

In order to eliminate the adverse affects of specular reflection apparatus has been constructed which incorporates a diffusing chamber or integrating sphere such as that set forth in U.S. Pat. No. 4,171,909. While such designs do provide diffuse light to illuminate a specimen the incorporation of an integrating sphere into such designs automatically increases the size and expense of the required optical readhead.

Another rather complicated and costly analyzer designed for textile color analysis is set forth in U.S. Pat. No. 4,033,698. In this design fiber optic bundles are utilized extensively for transmittal of light to and from a sample area. Aside from the expense of this design, the design does not effectively minimize stray light rays originating from a light source and thus the adverse affects of specular reflection.

The present invention is particularly directed to the construction of a small, reliable and inexpensive optical readhead for illuminating a reagent pad (specimen) and obtaining the measurement of nonspecular reflected light. Ideally, the overall outside dimensions of the reflectance instrument should be as small as possible such that it can be carried in a pocket or a purse. The present invention is directed to an optical readhead which not only permits construction of a reflectance instrument of very small dimensions, but achieves an optical S/N ratio which exceeds or at least is equal to 200:1.

SUMMARY OF THE INVENTION

In accordance with the present invention, a small, reliable and inexpensive optical readhead for illuminating a reagent pad and obtaining the measurement of nonspecular reflected light is disclosed in which controlled light rays are directed by means of a lens along a transmission path from a light source through a light trap to expose or illuminate a specimen and nonspecular reflected light is passed from the specimen though the light trap and a transmission path to one or more detectors where the nonspecular reflected light is measured. Thus, the light trap is positioned between the light source and the specimen and between the specimen and the detector(s). The resulting optical readhead can be made substantially smaller and more economically, without any decrease in reliability, than reflectance photometers commercially available.

BRIEF DESCRIPTION OF THE DRAWINGS

Other and further advantages and features of the invention will be apparent to those skilled in the art from the following detailed description thereof, taken in conjunction with the accompanying drawings, in which.

DESCRIPTION OF THE PREFERRED EMBODIMENTS

The apparatus forming the subject matter of the present invention involves at least one light source, at least one detector (e.g., photoelectric cell), a specimen holder and a light trap positioned between the detector(s) and specimen(s).

Figure 1:
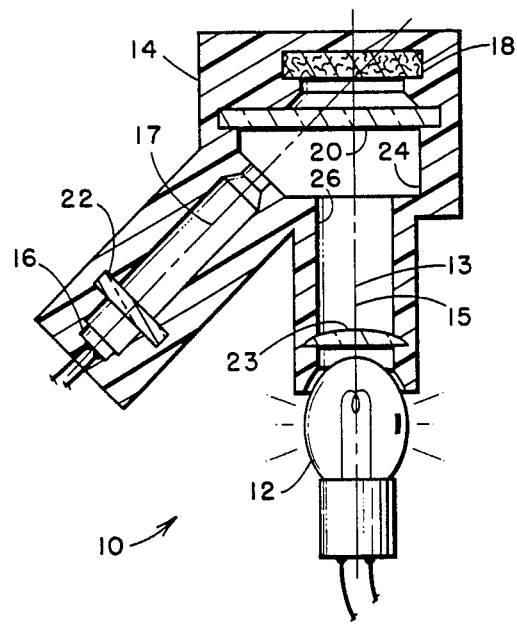
FIG. 1 is a schematic side view, in partial cross section, of apparatus in accordance with the present invention in which the axis of illumination is parallel to the normal of the specimen and the axis of detection is positioned at an angle 45 degrees to normal.

FIG. 1 of the drawings illustrates apparatus 10 for the measurement of reflectance. This apparatus includes a light source 12, a specimen holder 14 and reflected light detector 16. The axis of illumination 13 is parallel to an axis 15 which is normal to specimen 18.

In accordance with the present invention, the reflectance device 10 has a light trap 24 positioned between detector 16 and window 20 which protects specimen 18. The precise configuration of light trap 24 is not critical provided it is larger than light transmission path 26 from light source 12 to specimen 18 such that the walls of the light trap are not directly illuminated by the light source. The purpose of light trap 24 is to prevent stray light from passing to detector 16 off of the window which covers the specimen and also to prevents specular rays from passing from the specimen to the detector 16. The light trap also helps reduce secondary rays from baffles in the light transmission paths as the light rays pass from the light source through the light transmission path to illuminate the specimen and then pass from the specimen through another light transmission path to the detector. Advantageously, light trap 24 is coated with dull black paint and, if desired, the light trap can also contain baffles which help suppress stray light.

Figure 2:
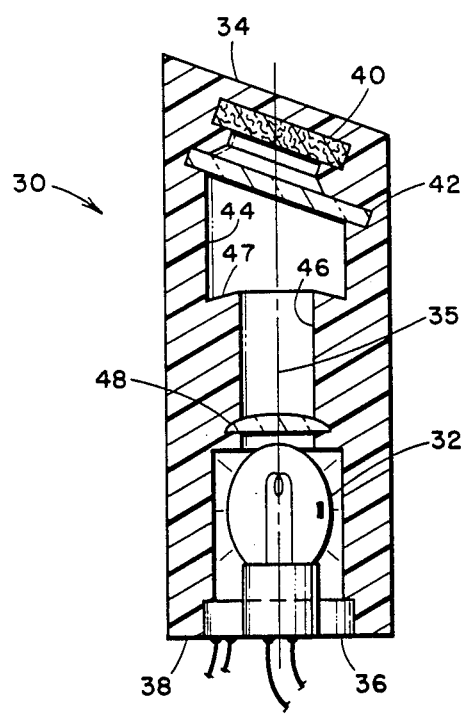
FIG. 2 is a schematic side view, in partial cross section, of another embodiment in accordance with the present invention in which the axes of illumination and detection are in one plane and the specimen is at an angle ($\phi$) to said plane.

FIG. 2 is a schematic illustration of another embodiment in accordance with the present invention comprising a reflectance device 30 composed of a light source 32, specimen holder 34 and a detector 36. Both light source 32 and detector 36 are mounted on the same surface 38 in close proximity to each other. Specimen holder 34 is positioned at an angle of approximately 20° with respect to the plane containing the axis of illumination and detection 35.

Specimen holder 34 holds specimen 40 in a position relative to window 42. Light trap 44 is positioned adjacent to window 42. Light transmission path 46 is of reduced diameter compared with light trap 44. Thus, light from light source 32 passes through light transmission path 46 and window 42 in order to illuminate specimen 40. Reflected light from specimen 40 returns through light transmission path 46 to detector 36. As emphasized in Ser. No. 438,010, filed Nov. 1, 1982, the presence of light source 32 and detector 36 mounted on the same plane 38 in close proximity to each other not only reduces the cost of the overall apparatus, requiring a less expensive construction, but it also facilitates miniaturization of the apparatus.

As in the case of light trap 24 in FIG. 1, light trap 44 of FIG. 2 can be coated with dull black paint and can contain baffles to facilitate the entrapment or suppression of stray light. Light trap 44 is shown with sloped walls 47—47 which also aid in suppressing stray light. Additionally, light transmission path 46 can contain threads or baffles to further minimize the passage of stray light to detector 36.

The specific light source(s) and detector(s) employed are not critical. One preferred light source is light emitting diode (LED) module HLMP-3950 made by Hewlett-Packard Components of Palo Alto, Calif. It will be understood, however, that the light source can be any suitable incandescent or nonincandescent light source provided a lens, such as integral lens 23 (FIG. 1) or 48 (FIG. 2), is employed to focus the light. Moreover, the light source can be frosted or used with diffusion means to cause diffuse illumination of the specimen. A suitable detector is model SD-041-11-11-011- (isolated)-211 which is made by Silicone Detector Corporation of Newbury Park, Calif. A filter 22 can, if desired, be placed in front of the detector.

Lens 23 and 48 serve two purposes. First of all, the lens focus much of the light over a short distance to maximize the light which is available to illuminate the specimen. In addition, the lens serve to control light transmitted to the specimen so as to minimize stray light, which will interfere with measurements being taken. It has been found, for example, that lens 23 reduces the extreme rays from a light source 12 from 40° (without the lens present) to 29° (with the lens). By combining lens 23 with light transmission path 26 the extreme rays from the light source are reduced to only 18° from the axis of illumination 13. Accordingly, the combination of a lens and the light transmission path are extremely effective for controlling stray rays and in obtaining nonspecular reflected light to be measured. It is this combination of a converging lens and the light transmission path together with a light trap which has resulted in the ability to reduce the size of the readhead by one-third that of presently available reflectance photometers and achieve cost savings of 20 to 30 percent without any deduction in reliability.

The dimensions of the light transmission path from the light source to the specimen are advantageously regulated such that the light passing along the axis of illumination 13 from light source 12 to the specimen 18 or along axis of illumination from light source 32 to sample 40 is within plus or minus 22 degrees of said axis and in which the light passed from specimen 18 or 40 to detector 16 or 36, respectively, along the axis of detection 17 or 35, respectively, is within plus or minus 6 degrees.

Figure 3:
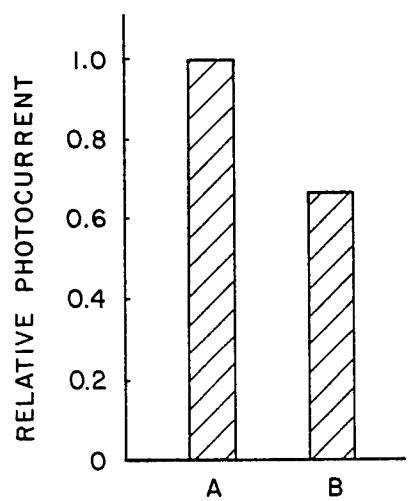
FIG. 3 is a bar graph illustrating relative photocurrents of prior art optical readheads (B) and readheads (A) having a construction in accordance with the embodiment illustrated in FIG. 1.
Figure 4:
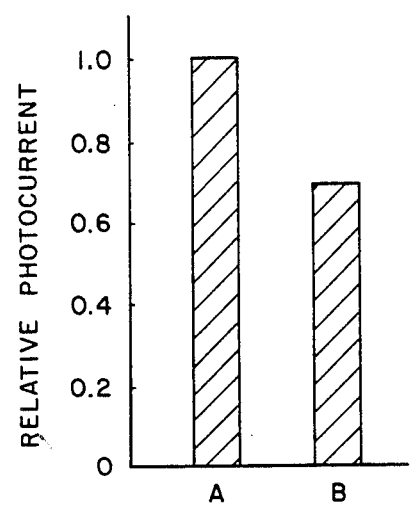
FIG. 4 is a bar graph illustrating relative photocurrents achieved utilizing optical readheads (A) and (B) when a scratched specimen window is present in the readheads.

The bar graphs in FIGS. 3 and 4 indicate the measured relative photocurrents of a prior art optical readhead (B) compared with the readhead (A) illustrated in FIG. 1. Clearly, as seen in FIG. 3, the optical readhead in accordance with present invention provides better throughput (in excess of 30 percent more photocurrent compared to the optical readhead without the controlled light rays). Moreover, as shown in FIG. 4, scratches on the specimen window are much less a factor when a light trap is present.

One way to compare the effectiveness of the disclosed embodiments is to measure the reflectance with and without controlled light rays and compare the resulting reflectance values to the reflectance of a dark pad. The accepted reflectance value for a "dark" (i.e., dull black) pad is 5.18 percent. Employing apparatus similar to that illustrated in FIG. 1 a reflectance of 4.77 percent was obtained whereas in a similar reflectance device without a light trap a reflectance value of 6.55 percent was obtained.

The material utilized in construction of the optical readhead is not critical; any suitable opaque material (e.g., metal or plastic) can be employed. Preferably, however, the optical readhead is constructed of a molded black plastic, such as an acrylonitrile-butadiene-styrene copolymer, polymethyl methacrylate, polystyrene, polyethylene, etc. As indicated above, the configuration of the light trap can be varied, but the light trap surface should not be directly illuminated by the light source employed. The lens and light transmission path of the present invention substantially eliminate stray light from illuminating the surface of the specimen.

By designing apparatus in accordance with the present invention small, inexpensive and reliable reflectance devices can be constructed. In fact, it has been found to be possible, utilizing the present invention, to construct an optical readhead which is about a third the size of that currently used in the GLUCOMETER reflectance photometer manufactured by the Ames Division of Miles Laboratories. Not only is the size reduced by about a third, but the cost of the optical readhead in accordance with the present invention results in a savings of at least 20 percent compared with the optical readhead utilized in the GLUCOMETER reflectance photometer. The substantial savings in size and in expense, without any decrease in reliability, are achieved due to the presence of the controlled light rays which permit the novel approach of the present invention to be taken.

From the foregoing, it will be seen that this invention is well adapted to attain all of the ends and objects hereinabove set forth, together with other advantages which are obvious and which are inherent to the system. Stray light rays originating from the light source or specimen are minimized in a manner which is convenient, simple, relatively inexpensive, positive, effective and reliable.

It should be understood that many variations within the skill of those in the art can be made, including the use of multiple light sources, the use of multiple detectors, the reversal in position of the light source and detector, the use of light sources differing in transmitted wave length, the use of filters to limit the light source transmitted or the reflected light detected, etc.

Obviously, many other modifications and variations of the inventions as hereinbefore set forth can be made without departing form the spirit and scope thereof.

What is claimed is:

1. Apparatus for measuring nonspecular reflected light which comprises a light source, means for supporting a specimen having a surface the reflectance of which is to be measured upon exposure to light emitted from said light source, and means for detecting light reflected from the surface of the specimen, wherein the apparatus is characterized by:

means defining a light illuminating transmission path in which the light source is located at one end thereof and the means for supporting the specimen having a surface the reflectance of which is to be measured is located at the opposite end thereof, said light illuminating transmission path containing a lens in front of said light source;

a light trap positioned at the end of the light illuminating transmission path opposite said light source and in front of said means for supporting the specimen having a surface the reflectance of which is to be measured; and means defining a light detection transmission path in which said light trap is located at one end and means for detecting light reflected from a surface of a specimen the reflectance of which is to be measured is located at the opposite end of said light detection transmission path;

wherein the combined effect of the lens and the light trap prevents specular reflected light from being transmitted through said light trap to said means for detecting light.

2. The apparatus of claim 1 in which the light trap includes light baffles.

3. The apparatus of claim 1 in which the light trap is positioned adjacent to a window covering the specimen.

4. The apparatus of claim 1 in which the light source is a incandescent lamp.

5. The apparatus of claim 4 in which the incandescent lamp has a diffusing surface.

6. The apparatus of claim 1 in which the light source is a light emitting diode.

7. The apparatus of claim 1 in which the optical signal to noise ratio is greater than or equal to 200:1.

8. The apparatus of claim 1 in which a filter is located in the light detection transmission path.

9. The apparatus of claim 1 in which the light emitted from said light source is maintained within ±22° of the axis of said light illuminating transmission path and in which light reflected from the surface of the specimen is maintained within ±6° of the axis of the light detection transmission path.

* * * * *